US010646366B2

(12) United States Patent
Pimentel et al.

(10) Patent No.: US 10,646,366 B2
(45) Date of Patent: May 12, 2020

(54) FUNCTIONAL SHOULDER SUPPORT BRACE WITH CABLING SYSTEM

(71) Applicants: Silas Efraim Bezerra de Araujo Pimentel, Holladay, UT (US); Austen David Archibald, West Jordan, UT (US); Bryce David Mortensen, Salt Lake City, UT (US)

(72) Inventors: Silas Efraim Bezerra de Araujo Pimentel, Holladay, UT (US); Austen David Archibald, West Jordan, UT (US); Bryce David Mortensen, Salt Lake City, UT (US)

( * ) Notice: Subject to any disclaimer, the term of this patent is extended or adjusted under 35 U.S.C. 154(b) by 481 days.

(21) Appl. No.: 15/478,131

(22) Filed: Apr. 3, 2017

(65) Prior Publication Data
US 2017/0281384 A1 Oct. 5, 2017

Related U.S. Application Data

(60) Provisional application No. 62/317,075, filed on Apr. 1, 2016.

(51) Int. Cl.
*A61F 5/01* (2006.01)
*A61F 13/14* (2006.01)
*A61F 5/05* (2006.01)

(52) U.S. Cl.
CPC .............. *A61F 5/0102* (2013.01); *A61F 5/05* (2013.01); *A61F 13/146* (2013.01)

(58) Field of Classification Search
CPC ........ A61F 5/01; A61F 5/0102; A61F 5/0104; A61F 5/0118; A61F 5/013; A61F 5/04; A61F 5/042; A61F 5/048; A61F 5/05841; A61F 5/05; A61F 5/058; A61F 5/05808; A61F 5/05858; A61F 5/37; A61F 5/3723; A61F 5/373; A61F 5/3738; A61F 5/3746; A61F 5/3753; A61F 13/146; A61F 5/00;
(Continued)

(56) References Cited

U.S. PATENT DOCUMENTS

| 5,403,268 A * | 4/1995 | Clement | ............... A61F 5/3738 |
| | | | 128/DIG. 19 |
| 7,954,204 B2 * | 6/2011 | Hammerslag | ............ A43B 5/16 |
| | | | 24/68 SK |

(Continued)

OTHER PUBLICATIONS

GivMohr Sling.
(Continued)

*Primary Examiner* — Victoria J. Hicks
*Assistant Examiner* — Lindsay A Jeffries
(74) *Attorney, Agent, or Firm* — Howard Russell (57) ABSTRACT

The present invention relates to a shoulder brace for the rehabilitation of patients that suffer from shoulder instability. The shoulder brace uses a novel elevation and compression cabling system to stabilize and approximate the humerus to glenoid fossa. More specifically, the present invention allows an individual that suffers from shoulder instability to easily put on and, while wearing the device, adjust all forces that approximate their shoulder without the assistance of another individual. The design will also allow the individual the ability to have functional movement. This will give someone who has become dependent on others to regain a greater degree of independence.

6 Claims, 9 Drawing Sheets

(58) Field of Classification Search
CPC .... A61F 5/0106; A61F 5/0123; A61F 5/0125;
A61F 5/0109; A61H 1/0274; A61H
1/0281; A61H 2205/06; A61H 2205/062;
A63B 21/4005; A63B 23/035; A63B
23/03508; A63B 23/12; A63B 23/1245;
A63B 23/1254; A63B 23/1263; A63B
23/1272; A63B 2023/006; A63B 21/4017;
A63B 21/4025; A41D 13/0512; A41D
27/10
USPC ......... 602/1, 5, 20; 601/5; 2/2.5, 16, 44, 45,
2/310, 459, 461, 462, 59
See application file for complete search history.

(56) References Cited

U.S. PATENT DOCUMENTS

| | | | | |
|---|---|---|---|---|
| 2010/0144490 A1* | 6/2010 | Purdy | ................ | A63B 21/0004 482/1 |
| 2010/0210985 A1* | 8/2010 | Kuorak | ................ | A61F 5/3723 602/20 |
| 2012/0101417 A1* | 4/2012 | Joseph | ................ | A61F 5/01 602/5 |
| 2013/0184627 A1* | 7/2013 | Vedder | ............... | A61B 17/1739 602/20 |
| 2013/0245522 A1* | 9/2013 | Modglin | ................... | A61F 5/01 602/16 |
| 2015/0247705 A1* | 9/2015 | Martinez | ................... | F41H 1/02 2/463 |

OTHER PUBLICATIONS

Rolyan Hemi Arm Sling.
Otto Bock Omo Neurexa.
DonJoy Shoulder Support.
Mcdavid 463.

\* cited by examiner

FUNCTIONAL SHOULDER SUPPORT BRACE WITH CABLING SYSTEM

CROSS-REFERENCE TO RELATED APPLICATION

This patent application claims the benefit and priority of U.S. Provisional Patent Application Ser. No. 62/317,075, for SHOULDER BRACE CABLING SYSTEM FOR PRODUCING ELEVATION AND COMPRESSION, filed 1 Apr. 2016.

FIELD OF THE INVENTION

The present invention relates to a shoulder brace with a cabling system for producing arm elevation and compression in individuals suffering from shoulder instability, and more particularly to a combination functional shoulder motion support brace comprising a cabling system for producing arm elevation and compression in individual users suffering from shoulder instability, the brace providing easy-to-use customizability of support (whether the brace is being worn or not by the user), the brace further providing approximation of a glenohumeral joint throughout motion functioning of the individual user's shoulder while wearing the brace, and the brace further providing ability for the individual user to don, fit, and customize the brace independently by individual use of a series of specialized closure systems with or without external assistance.

BACKGROUND OF INVENTION

Shoulder instability can occur in a number of scenarios. For instance, one of the most common residual effects faced by stroke victims is shoulder instability, caused by a subsequent decrease in neuromuscular tone and muscle strength. Of the nearly 800,000 people in the United States yearly who suffer a stroke, as many as 37% of survivors develop shoulder instability. Current shoulder braces require the wearer to either remove the brace to perform adjustments or have another person assist in making adjustments. Shoulder braces have been previously designed in two main ways.

The first, and most popular, method is through the use of a simple shoulder sling. Shoulder slings are designed intentionally shorter than the length of the wearer's upper arm so that, once fastened, the sling pushes the head of the humerus toward the glenohumeral joint to approximate normal shoulder function. However, a shoulder sling does not enable the wearer to simultaneously wear the device and adjust the amount of force applied to the arm. Therefore, adjusting a shoulder sling without first removing it requires an additional person and additional steps to perform the adjustment and re-installation on one's shoulder.

The second leading approach is to use a more extensive brace that provides a stable base around the trunk and upper shoulder and uses Velcro straps attached to an arm cuff that pulls the cuff towards the glenoid fossa. This method is even more difficult for the wearer to adjust. A person familiar with the brace must assist the individual to don and adjust the brace. The complexity and number of straps makes this design time consuming and difficult to adjust the forces acting on the arm and shoulder. Individuals using either of these designs often become dependent on others to properly put on and adjust the brace.

The present invention relating to a functional shoulder brace allows an individual suffering from shoulder instability to easily put on and, while wearing, adjust the fit to approximate normal shoulder function without the assistance of another individual. This will give individuals who suffer from shoulder instability a greater amount of independence, convenience and rehabilitation.

SUMMARY OF THE INVENTION

The figures and detailed description that follow exemplify various embodiments in accordance with various aspects of the invention. The present invention relates to a shoulder brace for the rehabilitation of patients suffering from shoulder instability. The shoulder brace uses a novel elevation and compression cable system to stabilize and approximate the shoulder. The present invention allows an individual that suffers from shoulder instability to easily put on and, while wearing the device, adjust all forces that approximate their shoulder without the assistance of another individual. The shoulder brace of the present invention will also allow the wearer the ability to have functional movement.

In one embodiment of the invention, the shoulder brace may comprise an elevation cable that is run through a first series of anchor points located primarily along the arm sleeve. The elevation cable is bound by a shoulder tightening mechanism, for instance a dial or cable-on-reel device, that is located near the top of the shoulder. The elevation cable is constricted by the shoulder tightening mechanism which in turn elevates the sleeve and leads the head of the humerus toward the glenoid fossa.

Similarly, a compression cable is run through a second series of anchor points located about the arm sleeve. The compression cable is bound by an arm tightening mechanism, for instance a dial or cable-on-reel device, that is located on the sleeve. The compression cable is constricted by the arm tightening mechanism causing the sleeve to compress around the wearer's arm.

By first compressing the sleeve around the wearer's arm, the elevation cable can effectively lift the arm without causing the sleeve to slip from the arm. In some embodiments, the second series of anchor points and the arm tightening mechanism are situated about the arm such that the compression cable is located on the front of the arm. Other embodiments feature the second series of anchor points and the arm tightening mechanism situated about the arm such that the compression cable is located on the side of the arm, or medially between posterior and anterior portions of the sleeve.

Some embodiments feature a sleeve cuff extending to below the elbow on the forearm, allowing for additional stability if needed. Additionally, in some embodiments, the compression cable is laced through the second series of anchor points in a crisscross fashion.

Thus, in accordance with an aspect and embodiment of the invention, there is provided a shoulder brace, comprising: a sleeve having a portion adapted for wearing over a user's shoulder and having another portion adapted for wearing over the user's upper arm below the user's shoulder. This aspect and embodiment of the invention further comprises a shoulder-tightening mechanism on the sleeve, a first series of anchor points located on the sleeve, an elevation cable passing through the first series of anchor points and bound by the shoulder-tightening mechanism such that the elevation cable is constricted by the shoulder-tightening mechanism in such a way that when the elevation cable is constricted by the shoulder-tightening mechanism, the sleeve of the shoulder brace is elevated.

Still further, this embodiment and aspect of the invention further preferably comprises an arm-tightening mechanism on the sleeve, a second series of anchor points located on the sleeve, a compression cable passing through the second series of anchor points and bound by the arm tightening mechanism such that the compression cable is constricted by the arm tightening mechanism to compress the sleeve.

In accordance with a second aspect of the invention, the second series of anchor points are located about the sleeve in such a way that when the compression cable is constricted by the arm-tightening mechanism, the sleeve is adapted to be compressed about a user's arm, enabling the sleeve to be lifted by the elevation cable without slipping from the user's arm. This aspect of the invention may be further enhanced wherein the compression cable is laced through the second series of anchor points in a crisscross fashion.

In accordance with another aspect and other embodiments of the invention, there is provided a shoulder brace, comprising: a first sleeve adapted for wearing over a user's shoulder, and a second sleeve, otherwise known as a sleeve cuff, adapted for wearing over the user's arm at a location below the user's shoulder. In this embodiment and aspect of the invention, there is further preferably provided an intermediate connecting sleeve portion interconnecting the first sleeve portion and the second sleeve portion. This intermediate sleeve portion protects the user's arm from contacting the cables, and it may also be made with a lighter weight fabric for breathability, flexibility, and ease of installation by the user.

In accordance with this aspect and embodiment of the invention, there is further provided a shoulder-tightening mechanism on the first sleeve, a first series of anchor points wherein a portion of the anchor points is located on the first sleeve and a portion of the anchor points is located on the second sleeve, and an elevation cable passing through the first series of anchor points and bound by the shoulder-tightening mechanism such that the elevation cable is constricted by the shoulder-tightening mechanism.

Still further, in accordance with this aspect and embodiment of the invention, there is provided an arm-tightening mechanism on the second sleeve, a second series of anchor points located on the second sleeve, and a compression cable passing through the second series of anchor points and bound by the arm tightening mechanism such that the compression cable is constricted by the arm tightening mechanism to compress the sleeve.

In this way, this aspect of the invention provides for a series of anchor points that are situated along the sleeve, or sleeves, in such a way that when the elevation cable is constricted by the shoulder-tightening mechanism, the sleeves of the shoulder brace are elevated, and thereby the user's humerus is elevated toward the user's glenoid fossa. This in turn serves in securing the user's arm and elevating his or her humerus into the glenoid fossa during whatever level of motion is allowed in accordance with a beneficial treatment protocol, and whether the brace is being worn, or before it has not yet been put on by the user. Further, this aspect and embodiment of the invention enables the user to more easily install the brace without any assistance from others.

Further, in accordance with this aspect of the invention, the second sleeve, or sleeve cuff, may be adapted in another embodiment to be located at below the user's elbow, to further stabilize the shoulder and further immobilize the arm. The shoulder brace of this aspect of the invention provides that the second series of anchor points may be located about the second sleeve in such a way that when the compression cable is constricted by the arm-tightening mechanism, the second sleeve is adapted to be compressed about a user's arm, enabling the sleeve to be lifted by the elevation cable without slipping from the user's arm. And in this way, the user's arm is held in an appropriate position relative to the glenoid fossa, regardless of allowed for movement of the shoulder or arm.

In accordance with another aspect of the invention, ease of use is enhanced by adaptations which make the brace of the present invention easier to put on and easier to adjust and customize, whether during use of the device or before. Thus, among other such ease-of-use attributes, there is provided that the second series of anchor points, the arm-tightening mechanism, and the compression cable may be located on an anterior portion of the sleeve or second sleeve, where they would be easier to reach by the user. Depending upon the application and the particular injury suffered by the user, the shoulder-tightening mechanism, the arm-tightening mechanism, the compression cable and/or the elevation cable may be, for ease of access by the user and to achieve desired forces supporting the arm and shoulder, located to a position between a posterior portion and an anterior portion of the sleeve.

Thus, the brace may be provided wherein the shoulder-tightening mechanism is located on the portion of the sleeve adapted for being worn over the user's shoulder, or it may be provided lower or more anteriorly as well for ease of access. Likewise, the brace may be provided, wherein the arm-tightening mechanism is located on the portion of the sleeve adapted for being worn over the user's upper arm.

In accordance with another aspect and embodiment of the invention, the shoulder brace preferably further comprises an outer layer of fabric for preventing the cables from catching on an exterior element of the user's environment. This provides an added level of safety for the user and his or her anticipated recovery.

In this and other embodiments and aspects of the invention, at least one of the shoulder-tightening mechanism and the arm-tightening mechanism, or both, may operate as a cable-on-reel device, such as may be provided with a BOA device from Boa Technology, Inc. of Denver, Colo., and described in U.S. Pat. No. 7,954,204 and No. 7,992,261, incorporated by reference in their entireties.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In consideration of the following detailed description of various embodiments, the invention may be more completely understood in connection with the following drawings.

Although the invention is amenable to various modifications and alternative forms, specifics thereof have been shown by way of example in the drawings and will be described in detail such that the disclosure will be thorough and complete, and will fully convey the scope of the invention to those skilled in the art. However, it should be understood, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The present invention relates to a shoulder brace for the rehabilitation of patients that suffer from shoulder instability. The shoulder brace uses novel elevation and compression cable systems to stabilize and approximate the glenohumeral joint through a range of motion particular to appropriate treatment parameters. More specifically, the present invention provides customizable support and approximation of the glenohumeral joint. Additionally, the present invention allows the individual to don, fit, and customize the shoulder brace independently using the elevation and compression cable systems, whether the brace is currently being worn by a user, or not.

Figure 1A:
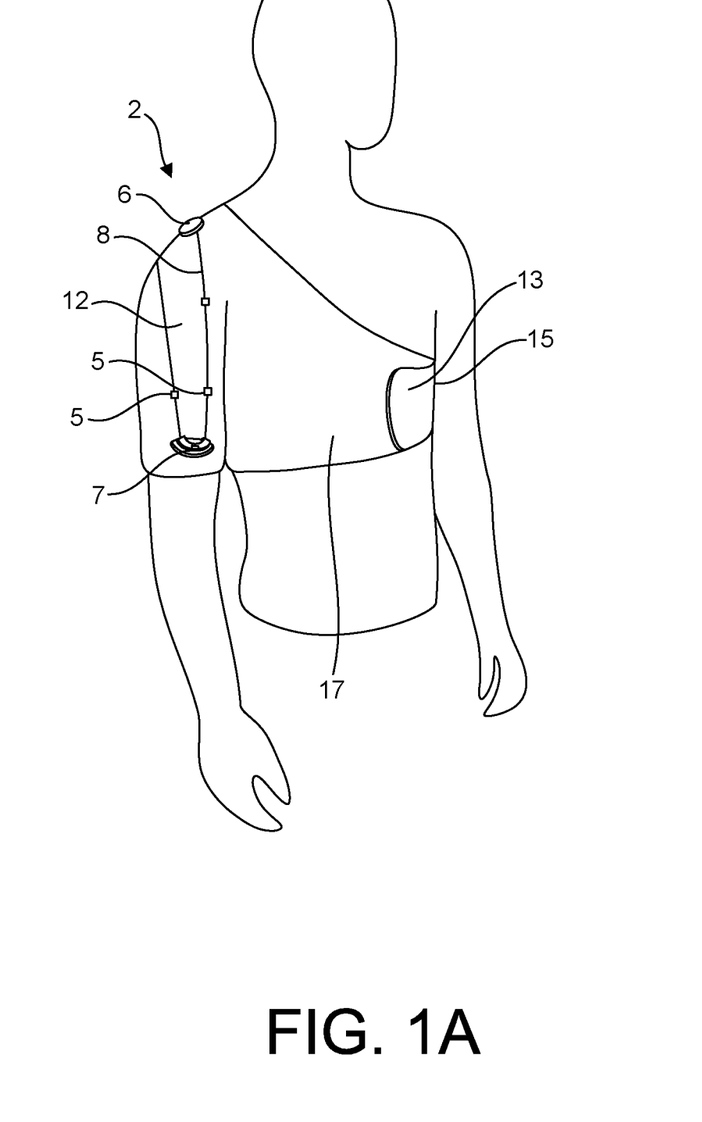
FIG. 1a is a perspective view of at least an aspect and an embodiment of the invention.
Figure 1B:
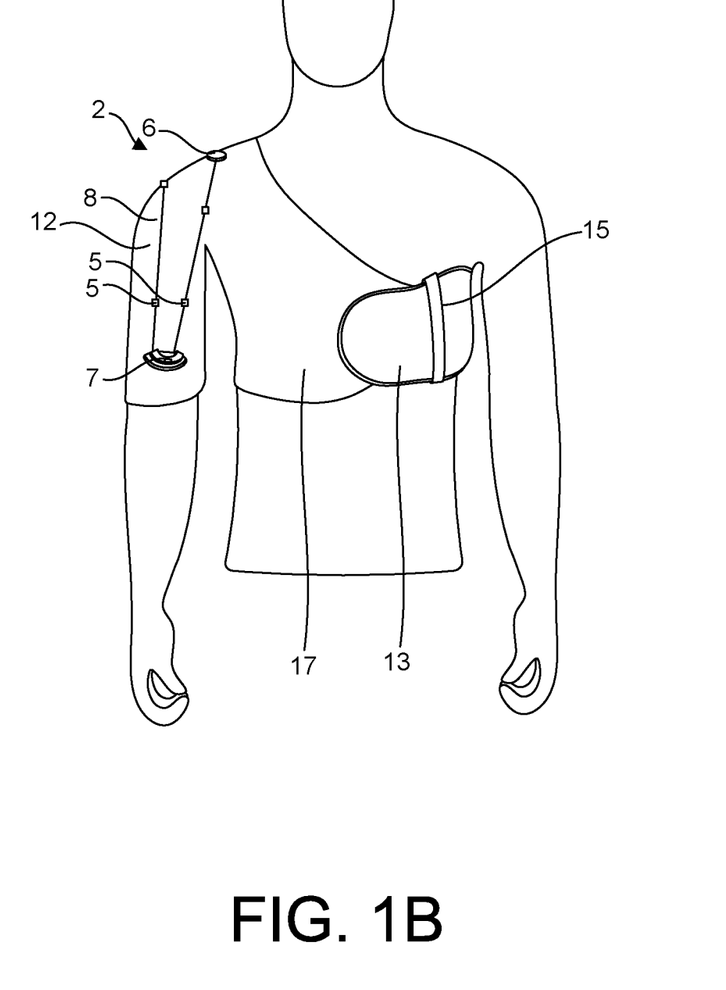
FIG. 1b illustrates the forces generated on a sleeve portion of the embodiment of FIG. 1a by an elevation cable according to that embodiment.

Referring specifically to FIGS. 1a and 1b, there is illustrated an embodiment of a shoulder brace 2 comprising a main body portion 17 for wearing by a user, or which is adapted for wrapping around, as with a strap 13, a user. The strap 13 is preferably provided with a hook and loop (e.g., Velcro brand) enclosure system 1 which works together with a retaining loop 15 to hold the brace 2 securely on the user. FIGS. 1a and 1b illustrate the forces generated on a sleeve 12 of the shoulder brace 2 by an elevation cable 8. According to this embodiment, a shoulder brace 2 is provided which may comprise an elevation cable 8 that runs or feeds through a first series of anchor points 5. The first series of anchor points 5 are located primarily along an arm sleeve 12 preferably with a lowermost anchor point 7 having a semi-circular guide portion for re-routing the cable 8 back and upwardly along the sleeve.

Each of the anchor points 5, and anchor point 7, serve as guides for smooth functioning of the cable while passing longitudinally through the guides and along the sleeve 12. Therefore the cable 8 may be free to run longitudinally, linearly, through guides of the anchor points 5, 7 (e.g., the anchor points may be lined with a nylon insert, or other suitable material, as a guide), as the cable is constricted, all the while being constrained (i.e., anchored) in one or more lateral directions to allow the creation of desired force characteristics (namely elevation, compression, and vector pull) for the brace 2 as shown. The sleeve 12 itself also serves to protect the wearer's arm from abrasive contact with the cable 8, and likewise an outer sleeve (not shown in FIG. 1a or FIG. 1b) may be employed to keep the cable 8 from catching on corners and the like in the wearer's environment while wearing the brace 2.

The elevation cable 8 is bound by a shoulder tightening mechanism 6, for instance a dial or cable-on-reel device, that is shown preferably located near the top of the sleeve 12. The elevation cable 8 is constricted by the shoulder tightening mechanism 6, as the shoulder tightening mechanism is dialed in the constricting rotational direction, and this in-turn elevates the sleeve 12 and leads the head of the wearer's humerus toward the wearer's glenoid fossa.

Figure 2:
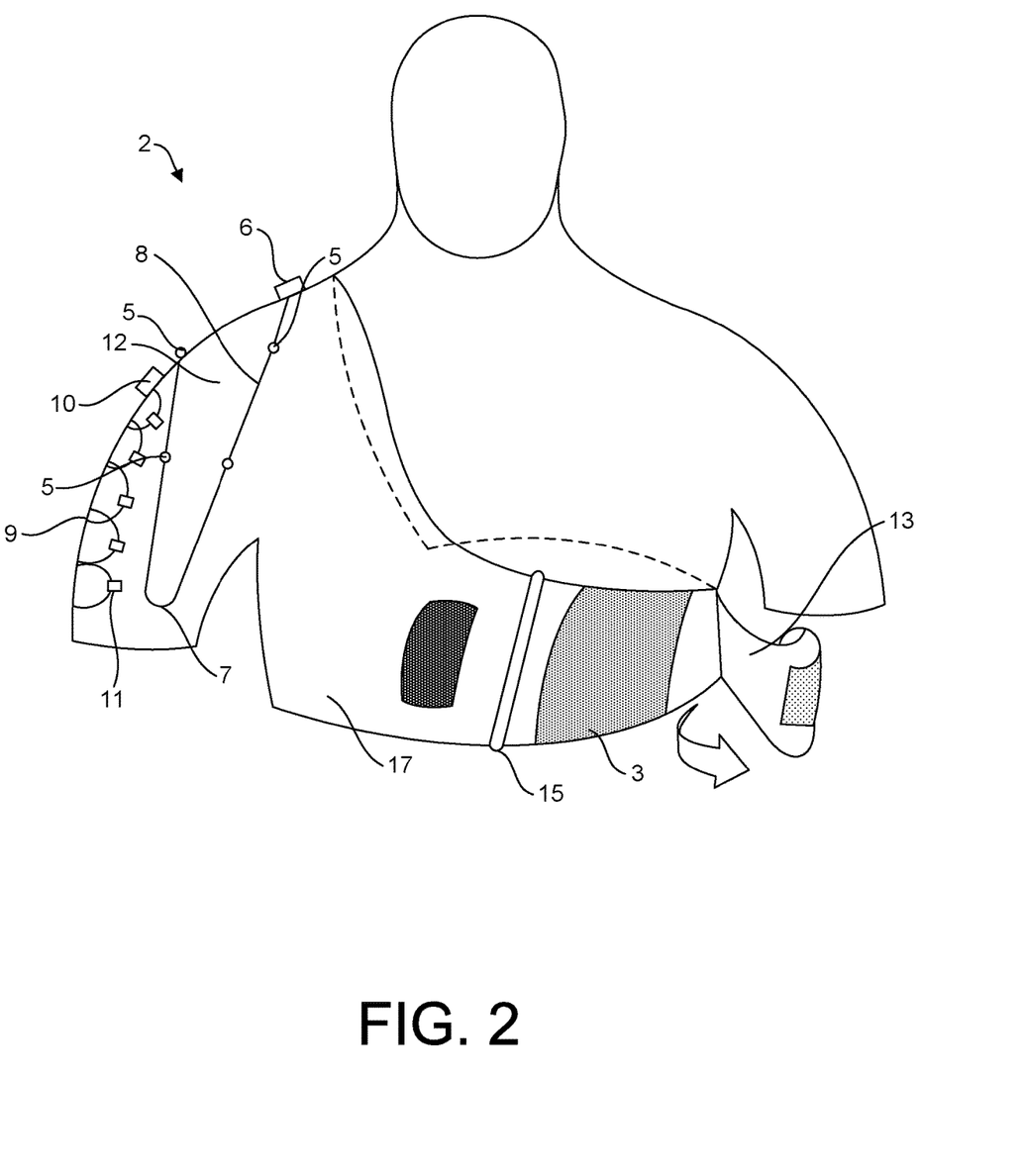
FIG. 2 illustrates a front view of at least an aspect of the present invention according to at least one embodiment.

FIG. 2 illustrates a front view of an embodiment of the invention similar to that shown and described in connection with FIGS. 1a and 1b, in that there is illustrated an embodiment of a shoulder brace 2 comprising a main body portion 10 for wearing by a user, or which is adapted for wrapping around, as with a strap 13, a user. The strap 13 is preferably provided with a hook and loop (e.g., Velcro brand) enclosure system 1 which works together with a retaining loop 15, and optional elastic portion 3, to hold the brace 2 securely on the user.

The brace 2 of FIG. 2 is similar to that of the brace 2 described in connection with FIGS. 1a and 1b, except that the brace 2 of FIG. 2 further illustrates the preferable addition of a separate arm-tightening mechanism 10, together with a second plurality, or series, of anchor points 11 with guides, and which has a compression cable 9 passing through each of the anchor points 11. Thus, as with the shoulder brace 2 of FIGS. 1a and 1b, there is provided a shoulder brace 2 having a sleeve 12 having attached to a surface thereof, as with glue, or by sewing or riveting, a plurality of, or series of, anchor points 5.

The first series of anchor points 5 are located primarily along the arm sleeve 12 preferably with a lowermost anchor point 7 having a semi-circular guide portion for re-routing the cable 8 back and upwardly along the sleeve. Each of the anchor points 5, and anchor point 7, as well as each of the second series of anchor points 11, serves as a guide for smooth functioning of the respective cables, 8 and 9 running therethrough, and longitudinally along the sleeve 12. Therefore the cables 8 and 9 are free to run longitudinally, linearly, through guides of the anchor points 5, 7 and/or 11 (e.g., the anchor points are preferably lined with a nylon, or other suitable material, insert as a guide), as the cable is constricted, all while being constrained (i.e., anchored) in one or more lateral directions to allow the creation of desired force characteristics (namely elevation, compression, and vector pull) for the brace 2.

The sleeve 12 itself also serves to protect the wearer's arm from abrasive contact with the cables 8 and 9, and likewise an outer sleeve (not shown in FIG. 2) may be employed to keep the cables 8 and 9 from catching on corners and the like in the wearer's environment while wearing the brace 2.

The elevation cable 8 is bound by a shoulder tightening mechanism 6, for instance a dial or cable-on-reel device, that is shown preferably located near the top of the sleeve 12. The elevation cable 8 is constricted by the shoulder tightening mechanism 6, as the shoulder tightening mechanism is dialed by the user, or wearer, in the constricting rotational direction, and this in-turn elevates the sleeve 12 and leads the head of the wearer's humerus toward the wearer's glenoid fossa.

Non-slippage of the brace 2 along a user's arm is facilitated by tightening of the arm-tightening mechanism 10 before tightening of the shoulder tightening mechanism 6, thus assuring that the entire arm is held in proper position relative to the glenohumeral joint, to allow circumscribed movement in a beneficial range of motion according to a treatment plan.

Figure 3:
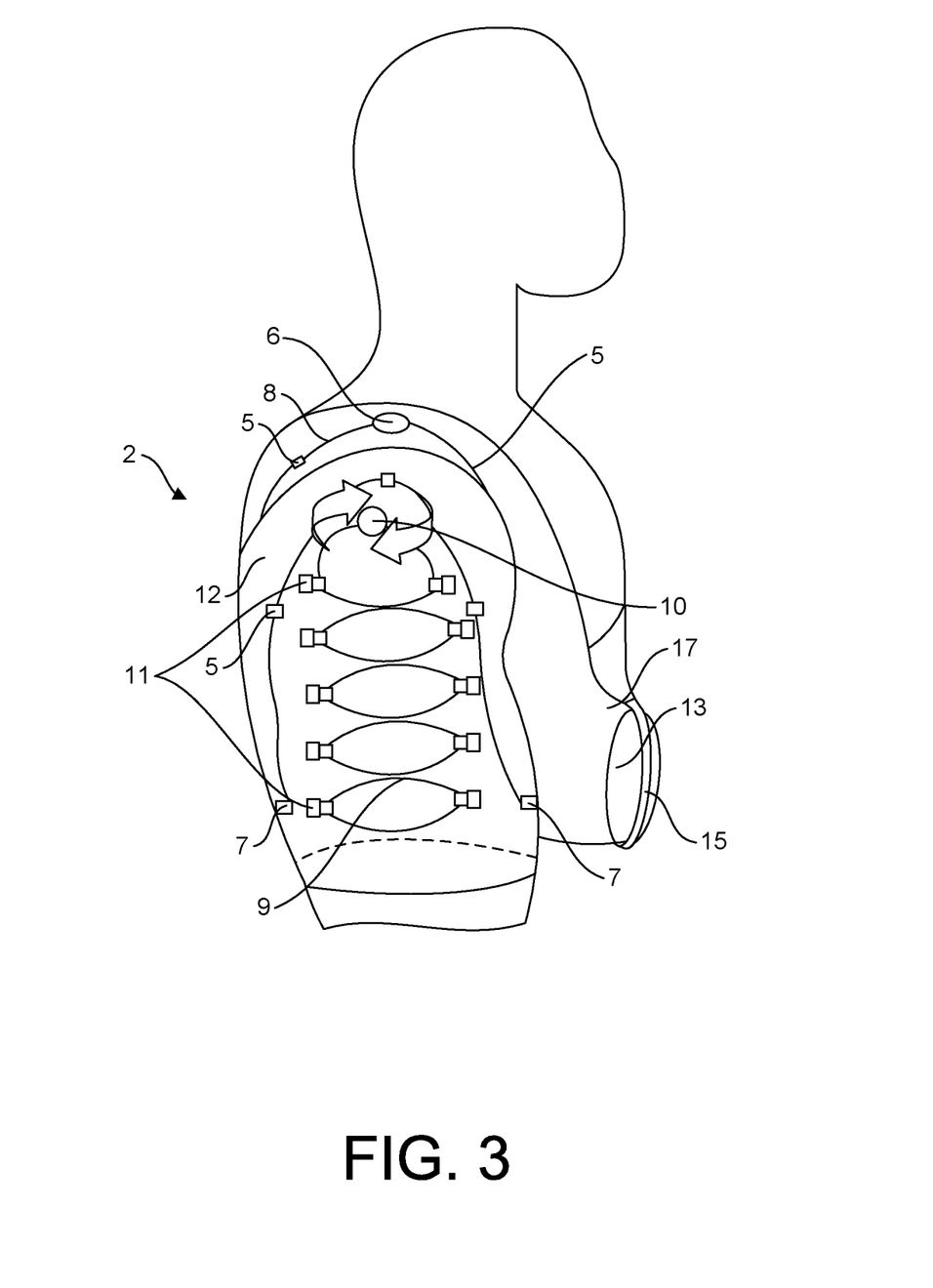
FIG. 3 illustrates a lateral view of the elevation cable system and the compression cable system according to at least one embodiment.

FIG. 3 illustrates a lateral-view of the elevation cable system (comprised of shoulder-tightening mechanism 6, cable 8, and anchor points 5 and 7) and the compression cable system (comprised of arm-tightening mechanism 10, cable 9, and anchor points 11) according to an embodiment of the shoulder brace 2. The compression cable 9 is run through the second series of anchor points 11 located about the arm sleeve 12. The compression cable 9 is bound by an arm tightening mechanism 10, for instance a dial or cable-on-reel device, which is located on the sleeve 12. The compression cable 9 is constricted by the arm tightening mechanism 10 which in turn compresses the sleeve 12 around the wearer's arm. By first compressing the sleeve 12 about the wearer's arm, the elevation cable 8 can effectively lift the arm without causing the sleeve 12 to slip along the wearer's arm.

Suitable tightening mechanisms include various cable-on-reel devices such as those available under the name BOA from Boa Technology, Inc. of Denver, Colo., and described in U.S. Pat. No. 7,954,204 and No. 7,992,261, incorporated by reference in their entireties.

Figure 4:
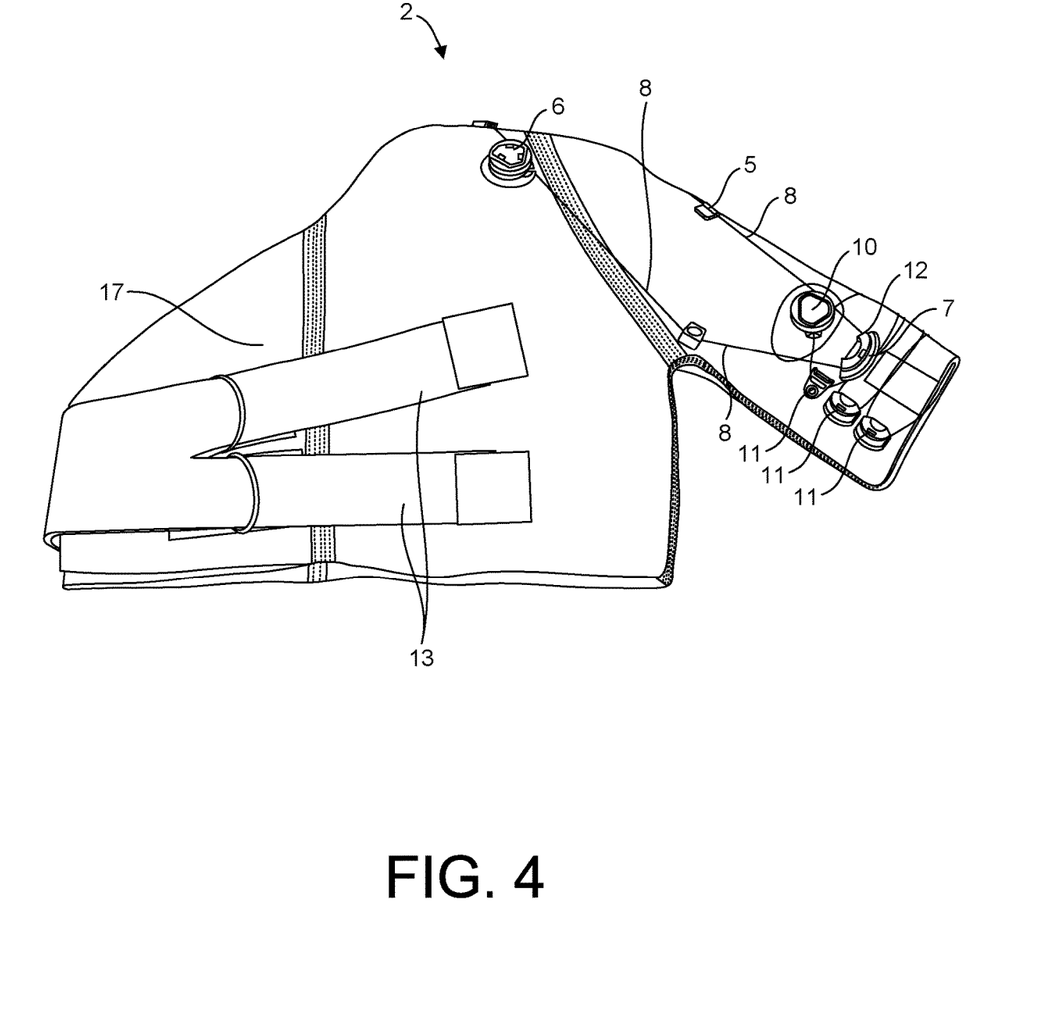
FIG. 4 shows a front view of the elevation cable system, the compression cable system, and the trunk straps according to at least one embodiment.
Figure 5:
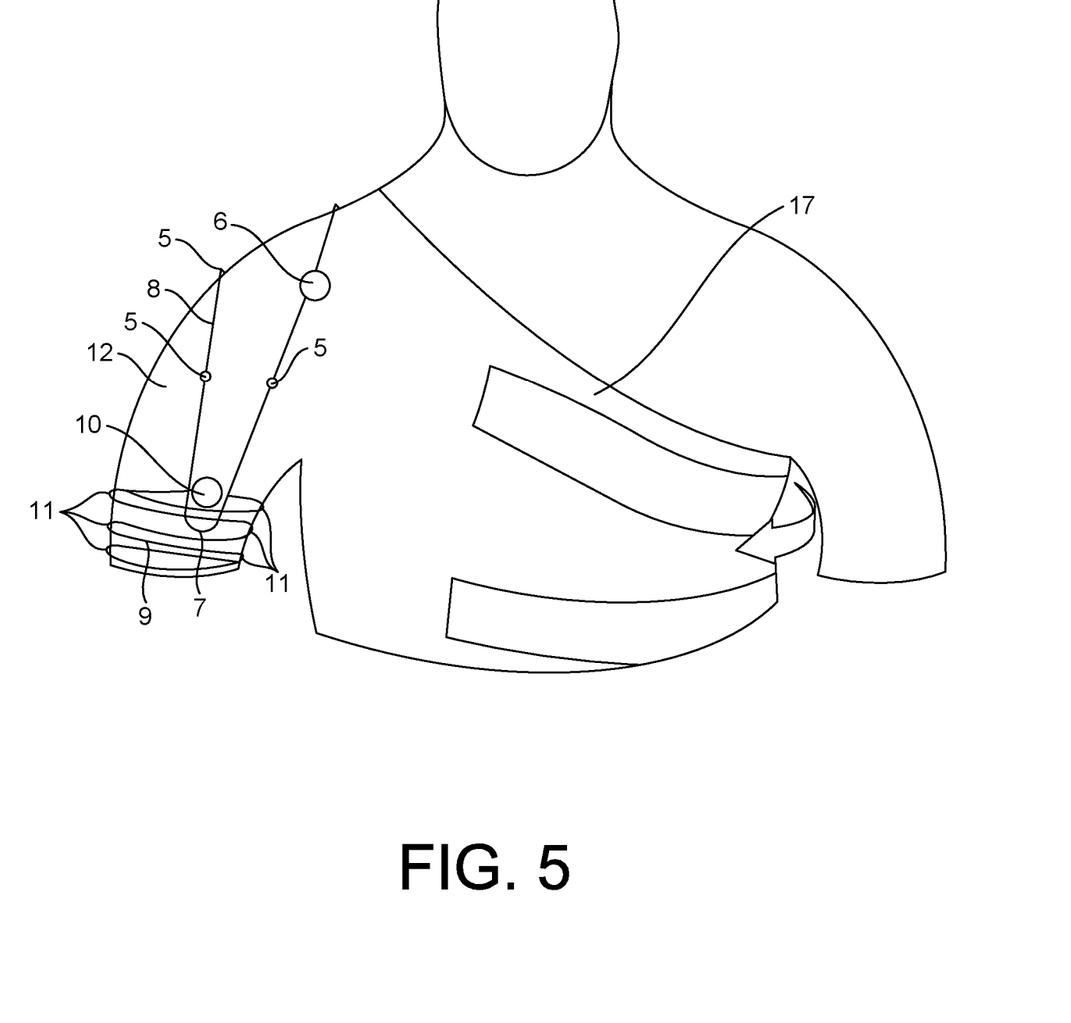
FIG. 5 illustrates a front view of the shoulder brace, wherein the compression cable system is located on the front of the arm according to at least one embodiment.
Figure 6:
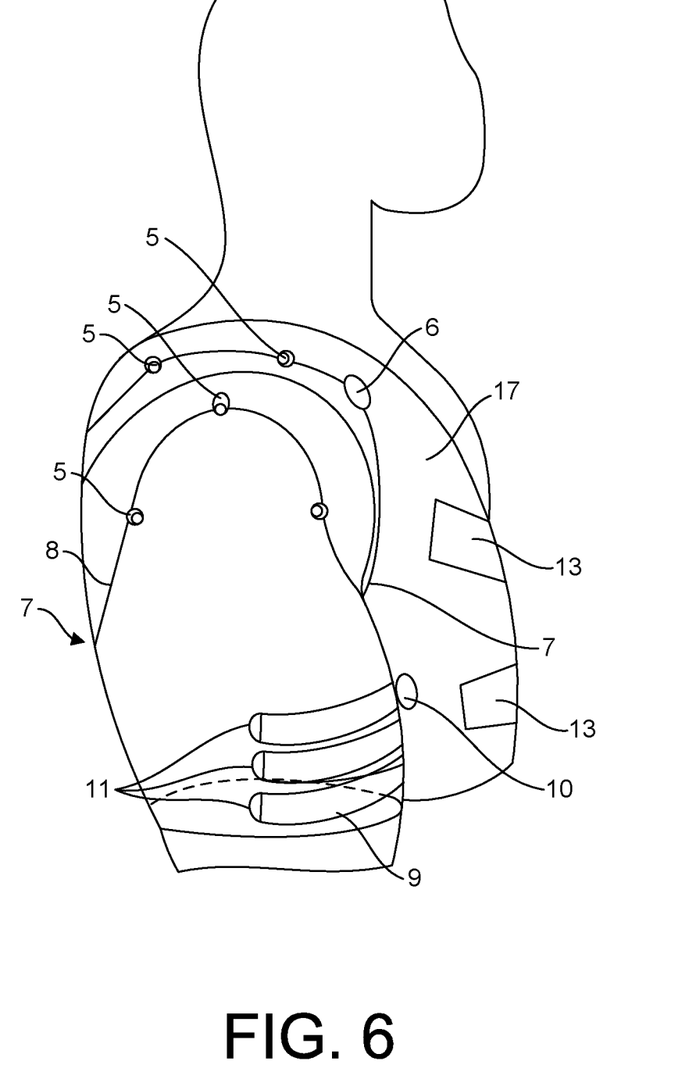
FIG. 6 illustrates a lateral view of the shoulder brace, wherein the arm compression cable system is located on the front of the arm according to at least one embodiment.

As illustrated in FIG. 4, FIG. 5, and FIG. 6, some embodiments feature the second series of anchor points 11 and arm tightening mechanism 10 situated such that the compression cable 9 is located on the front of the arm. Some embodiments feature the second series of anchor points 11 and arm tightening mechanism 10 situated such that compression cable 9 is located on the side of the arm, as illustrated in FIG. 2 and FIG. 3. Some embodiments feature a separate sleeve, or cuff, 19 extending to just above the elbow on the forearm (see FIG. 7) or alternatively extending to below the elbow on the forearm (see FIG. 8), allowing for additional stability if needed. Additionally, in some embodiments, the compression cable 9 is laced through the second series of anchor points 11 in a crisscross fashion as illustrated in FIG. 3.

Figure 7:
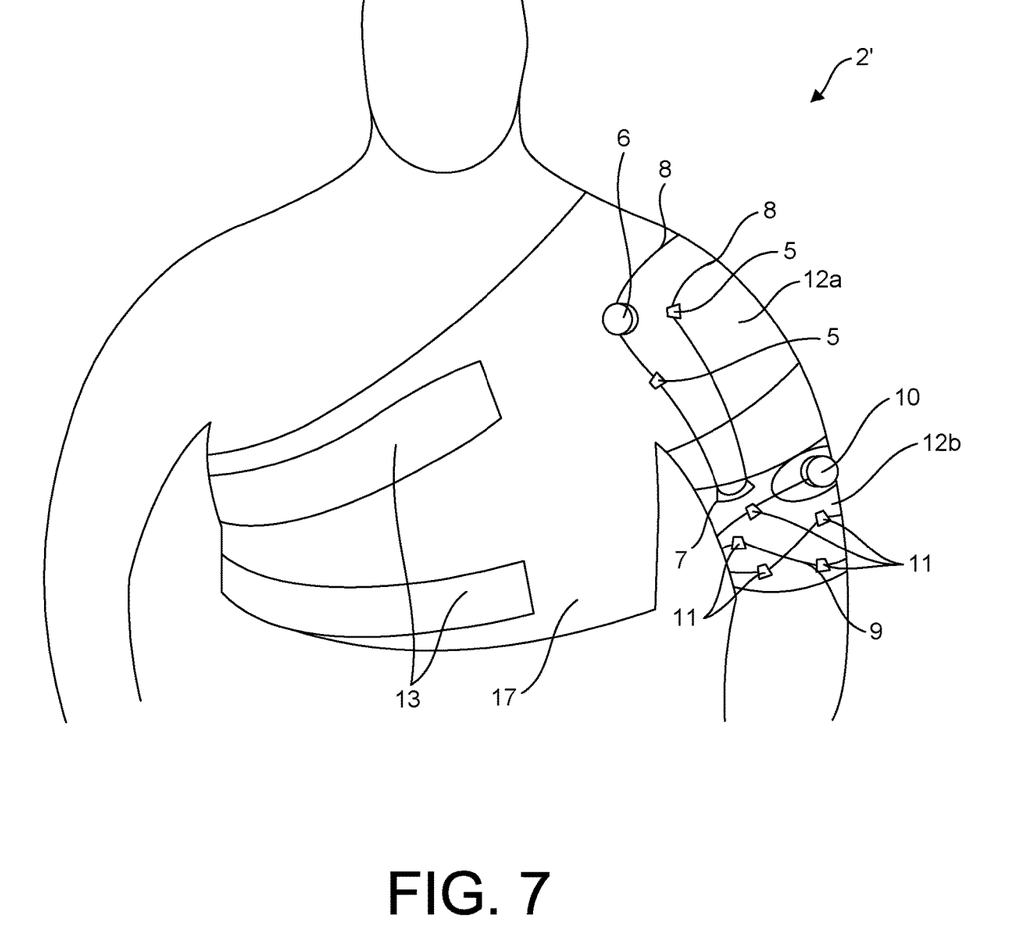
FIG. 7 illustrates an alternative embodiment of the shoulder brace, wherein an arm compression portion of the brace is located just above a user's elbow and is separated from an upper-sleeve compression portion of the brace with lighter-weight fabric designed to protect the user's arm from abrasive contact with cabling extending between the two portions.

Referring now specifically to FIG. 7, there is provided an alternative embodiment of a shoulder brace 2' comprising a separate arm sleeve 12b (in addition to a shoulder sleeve 12a), which is adapted to be located on, to cover just above, the elbow of the user. Wherein, as with the other embodiments herein described, there is provided the elevation cable system (comprised of a shoulder-tightening mechanism 6, a cable 8, and anchor points 5 and 7) and a compression cable system (comprised of an arm-tightening mechanism 10, a cable 9, and anchor points 11). The compression cable 9 passes through the second series of anchor points 11 located about the arm sleeve 12b. The compression cable 9 is bound by the arm tightening mechanism 10, for instance a ratcheting/easy-releasing dial or cable-on-reel device, which is located on the sleeve 12b. The compression cable 9 is constricted by the arm tightening mechanism 10 which in turn compresses the sleeve 12b around the wearer's arm. By first compressing the sleeve 12b about the wearer's arm, the elevation cable 8 can then more effectively lift the arm without causing the sleeve 12b to slip along the wearer's arm.

The cable 8 of the elevation cable system of shoulder brace 2' extends from the sleeve 12a down to sleeve 12b adapted to be located just above the user's elbow, as the cable runs through upper anchor points 5 on sleeve 12a and lower anchor point 7 on sleeve 12b. In this manner, after the sleeve 12b is compressed about the wearer's arm, the cable elevation system is more effective in elevating the arm, and particularly the humerus of the arm, into proper location relative to the glenohumeral joint of the user. This elevated position is able to be maintained during movement of the user's arm, and this position may be achieved both by adjusting the elevation cable system before putting on the brace 2', or even after putting on the brace. In this way the system is fully customizable to the user's needs.

Figure 8:
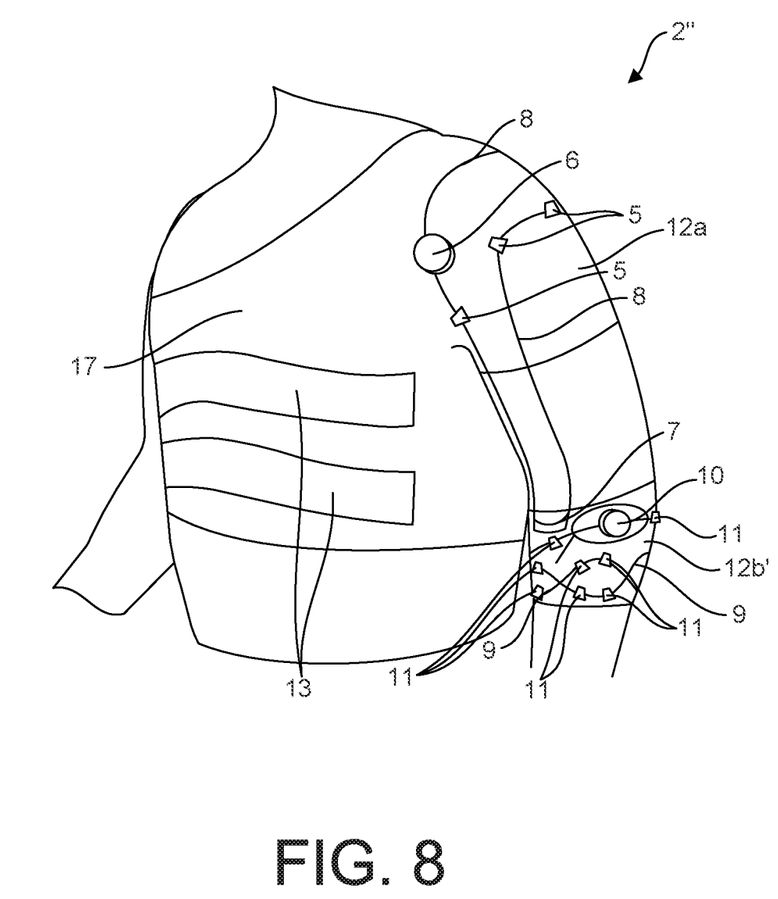
FIG. 8 illustrates an alternative embodiment of the shoulder brace, wherein an arm compression portion of the brace is located just below a user's elbow to provide greater stability and is separated from an upper-sleeve compression portion of the brace with lighter-weight fabric designed to protect the user's arm from abrasive contact with the cabling extending between the two portions.

Referring now specifically to FIG. 8, there is provided yet another alternative embodiment of a shoulder brace 2" comprising a separate arm sleeve 12b' (in addition to a shoulder sleeve 12a), which is adapted to be located on, to cover, the user's arm just below the elbow. Wherein, as with the other embodiments herein described, there is provided the elevation cable system (comprised of a shoulder-tightening mechanism 6, a cable 8, and anchor points 5 and 7) and a compression cable system (comprised of an arm-tightening mechanism 10, a cable 9, and anchor points 11). The compression cable 9 is run through the second series of anchor points 11 located about the arm sleeve 12b'. The compression cable 9 is bound by an arm tightening mechanism 10, for instance a dial or cable-on-reel device, which is located on the sleeve 12b'. The compression cable 9 is constricted by the arm tightening mechanism 10 which in turn compresses the sleeve 12b' around the wearer's arm. By first compressing the sleeve 12b' about the wearer's arm, the elevation cable 8 can then more effectively lift the arm without causing the sleeve 12b to slip along the wearer's arm.

The cable 8 of the elevation cable system of shoulder brace 2" extends from the sleeve 12a down to sleeve 12b' adapted to be located just below the user's elbow, as the cable runs through upper anchor points 5 on sleeve 12a and lower anchor point 7 on sleeve 12b'. In this manner, after the sleeve 12b' is compressed about the wearer's arm by tightening with the compression cable system, the cable elevation system is more effective in elevating the arm, and particularly the humerus of the arm, into proper location relative to the glenohumeral joint of the user (because slippage of the sleeve 12b around the arm is prevented). This position is able to be maintained during movement of the user's arm, and this position may be achieved both by adjusting the elevation cable system before putting on the brace 2", or even after putting on the brace. In this way the system is fully customizable to the user's needs, and with the lower sleeve, or cuff, 12b' even further stability and immobilization may be provided if desired.

The present invention allows an individual that suffers from shoulder instability to easily put on and adjust all forces that approximate their shoulder while wearing the brace and without the assistance of another individual. The design will also allow the individual the ability to have functional movement. This will give someone who has become greatly dependent on others to regain a greater amount of their independence.

The present invention may be embodied in other specific forms without departing from its spirit or essential characteristics. The described embodiments are to be considered in all respects only as illustrative and not restrictive. All changes that come within the meaning and range of equivalency of the claims are to be embraced within their scope.

The various components of the present invention may be constructed generally out of any materials known to be suitable in the art.

Many modifications and other embodiments of the invention set forth herein will come to mind to one skilled in the art to which this invention pertains and having the benefit of the teaching presented in the foregoing descriptions and the associated drawings. Therefore, it should be understood that the inventions are not to be limited to the specific embodiments disclose and that modifications and other embodiments are intended to be included within the scope of the appended claims.

What is claimed is:

1. A shoulder brace, comprising:
  a sleeve having a portion adapted for wearing over a user's glenohumeral joint, and having another portion adapted for wearing over the user's humerus;
  a first reel or dial mounted on said sleeve at a location over the portion of the sleeve adapted for wearing over the user's glenohumeral joint;
  a first series of anchor points located on said sleeve at locations adapted to be positioned above and below the user's glenohumeral joint;
  an elevation cable passing through said first series of anchor points such that said elevation cable is able to be constricted by operation of said first reel or dial;
  a second reel or dial mounted on the portion of said sleeve adapted for wearing over the user's humerus;
  a second series of anchor points located on the portion of said sleeve adapted for wearing over the user's humerus; and
  a compression cable passing through said second series of anchor points and able to be tightened by said second reel or dial such that said compression cable is able to be constricted by said second reel or dial to compress said sleeve such that also operating said first reel or dial is adapted to elevate the user's humerus toward the user's glenohumeral joint;
  wherein the first reel or dial and the second reel or dial are positioned on a front of the shoulder brace as to allow for self-adjustment by the user, without assistance of another person,
  wherein the first reel or dial allows for independent adjustment of the elevation cable, and
  wherein the second reel or dial allows for independent adjustment of the compression cable.

2. The shoulder brace of claim 1, wherein said first series of anchor points are situated along said sleeve in such a way that when said elevation cable is constricted by said first reel or dial, said sleeve of the shoulder brace is elevated.

3. The shoulder brace of claim 1, wherein said second series of anchor points are located about said sleeve in such a way that when said compression cable is constricted by said second reel or dial, the sleeve is adapted to be compressed about a user's arm, enabling said sleeve to be lifted by said elevation cable without slipping from the user's arm.

4. The shoulder brace of claim 1, wherein said compression cable is laced through said second series of anchor points in a crisscross fashion.

5. The shoulder brace of claim 1, wherein said second series of anchor points, said second reel or dial, and said compression cable are located on an anterior portion of said sleeve.

6. A shoulder brace, comprising:
  a sleeve having a portion adapted for wearing over a user's glenohumeral joint and having another portion adapted for wearing over the user's humerus;
  a first reel or dial mounted on said sleeve at a location over the portion of the sleeve adapted for wearing over the user's glenohumeral joint;
  a first series of anchor points located on said sleeve at locations adapted to be positioned above and below the user's glenohumeral joint;
  a cable passing through said first series of anchor points such that said cable is able to be constricted by operation of said first reel or dial;
  a second reel or dial mounted on the portion of said sleeve adapted for wearing over the user's humerus; and
  a second series of anchor points located on the portion of said sleeve adapted for wearing over the user's humerus;
  wherein operating said first reel or dial is adapted to elevate the user's humerus toward the user's glenohumeral joint,
  wherein the first reel or dial and the second reel or dial are positioned on a front of the shoulder brace as to allow for self-adjustment by the user, without assistance of another person.

* * * * *